United States Patent [19]

Hokama

[11] 4,443,248

[45] Apr. 17, 1984

[54] PHENOXYPHENOXYPROPIONIC ACIDS AND DERIVATIVES, AND THEIR USE AS HERBICIDES

[75] Inventor: Takeo Hokama, Chicago, Ill.

[73] Assignee: Velsicol Chemical Corporation, Chicago, Ill.

[21] Appl. No.: 367,642

[22] Filed: Apr. 12, 1982

[51] Int. Cl.³ .................. C07C 149/40; A01N 37/00; A01N 31/00; C07C 149/40
[52] U.S. Cl. .......................... 71/98; 560/17; 260/455 R; 71/100; 71/105; 71/118; 564/162; 562/432; 260/465 D
[58] Field of Search ............ 562/427, 432; 560/17; 260/455 R, 465 E, 465 F, 465 D; 71/100, 98; 564/27, 162

[56] References Cited

U.S. PATENT DOCUMENTS 4,070,177 1/1978 Nishiyama et al. ............ 260/455 R

FOREIGN PATENT DOCUMENTS 1641 10/1978 Fed. Rep. of Germany ... 260/455 R

OTHER PUBLICATIONS

Schonowsky et al., Z. Naturforsch; Nitrodiphenylethers, Herbicides; pp. 902–908.

*Primary Examiner*—Henry R. Jiles
*Assistant Examiner*—Robert C. Whittenbaugh
*Attorney, Agent, or Firm*—Robert J. Schwarz

[57] ABSTRACT

This invention discloses novel herbicidal compounds of the formula

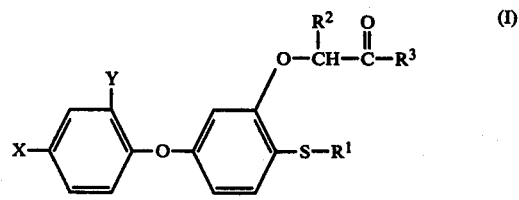

wherein X is selected from the group consisting of halogen, nitro, cyano and trifluoromethyl; Y is selected from the group consisting of hydrogen, halogen, nitro and cyano; $R^1$ is alkyl; $R^2$ is selected the group consisting of hydrogen and alkyl; and $R^3$ is selected from the group consisting of hydroxy, alkoxy, alkylthio, amino, alkylamino and dialkylamino and further herbicidal compositions and methods using said compounds.

12 Claims, No Drawings

PHENOXYPHENOXYPROPIONIC ACIDS AND DERIVATIVES, AND THEIR USE AS HERBICIDES

This invention relates to new compositions of matter and more specifically relates to new chemical compounds of the formula

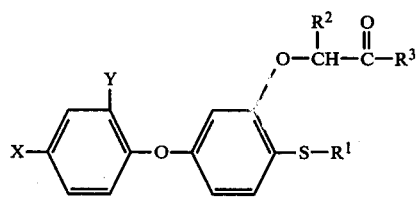

wherein X is selected from the group consisting of halogen, nitro, cyano and trifluoromethyl; Y is selected from the group consisting of hydrogen, halogen, nitro and cyano; $R^1$ is alkyl; $R^2$ is selected from the group consisting of hydrogen and alkyl; and $R^3$ is selected from the group consisting of hydroxy, alkoxy, alkylthio, amino, alkylamino and dialkylamino. Further, the present invention is directed to alkali metal, alkaline earth metal, ammonium, mono-, di- and trialkylamine and mono-, di- and trialkanolamine salts of the compounds of formula I wherein $R^3$ is hydroxy.

The compounds of the present invention are unexpectedly useful as selective herbicides.

In a preferred embodiment of the present invention X is selected from the group consisting of chlorine, bromine, fluorine, nitro, cyano, and trifluoromethyl; Y is selected from the group consisting of hydrogen, chlorine, bromine, nitro and cyano; $R^1$ is lower alkyl; $R^2$ is hydrogen or lower alkyl; and $R^3$ is selected from the group consisting of hydroxy, lower alkoxy; lower alkylthio, amino, lower alkylamino and di(loweralkyl)amino; and further, the sodium, potassium, calcium, ammonium, the lower mono-, di- and trialkylamine and the lower mono-, di- and trialkanolamine salts of the compounds of formula I wherein $R^3$ is hydroxy. The term lower as used herein designates a straight or branched carbon chain of 1 to 6 carbon atoms.

The compounds of the present invention can be prepared by reacting an alkali metal phenolate of the formula

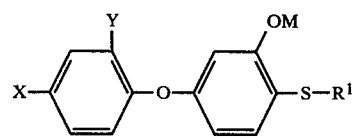

wherein M is an alkali metal such as sodium or potassium and X, Y and $R^1$ are as heretofore described, with an alpha bromo compound of the formula

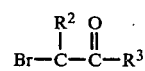

wherein $R^2$ and $R^3$ are as heretofore described. This reaction can be readily effected by combining the reactants in an inert organic reaction medium such as dimethylsulfoxide at room temperature. The reaction mixture can be agitated for a period of from 1 to 8 hours to ensure completion of the reaction. Equimolar or slight excess molar amounts of the compound of formula III can be employed. After completion of the reaction the mixture can be washed with water to remove alkali metal bromide that is formed and can thereafter be stripped of solvent or further purified if desired to yield the compounds of the present invention.

The alkali metal phenolate of formula II can be prepared in situ in the foregoing reaction by combining the reactants in the presence of sodium or potassium carbonate.

The compounds of the present invention wherein $R^3$ is hydroxy are preferably prepared by hydrolyzing a corresponding lower alkyl ester such as the ethyl ester by standard techniques.

The free phenols corresponding to the structure of formula II can be prepared by reacting a compound of the formula

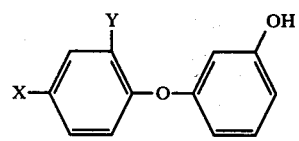

wherein X and Y are as heretofore described, with an excess molar amount of an alkyl sulfenyl chloride of the formula

wherein $R^1$ is as heretofore described. This reaction can be effected by slowly combining solution of the reactants in an inert organic solvent such as methylene chloride at a temperature below about 0° C. The reaction mixture can be stirred first at the cooled temperature and thereafter at room temperature to ensure completion of the reaction. The reaction mixture can then be washed with dilute aqueous base and water and can thereafter be stripped of solvent to yield the desired product.

Exemplary suitable compounds of formula III for preparing the compounds of the present invention are 3-(2-chloro-4-trifluoromethylphenoxy) phenol, 3-(2-bromo-4-trifluoromethylphenoxy)phenol, 3-(2-nitro-4-trifluoromethylphenoxy)phenol, 3-(2-cyano-4-trifluoromethylphenoxy) phenol, 3-(2-chloro-4-nitrophenoxy)phenol, 3-(2-chloro-4-cyanophenoxy)phenol, 3-(2,4-dichlorophenoxy)phenol, 3-(2,4-dibromophenoxy)phenol, 3-(4-fluorophenoxy)phenol.

The metal salts of the compounds of the present invention can be readily prepared by reacting the free acid of the desired compound with the hydroxide of the desired metal utilizing standard techniques. Similarly, the ammonium, amine and alkanolamine salts of the compounds of this invention can be prepared from the corresponding acid.

The manner in which the compounds of the present invention can be prepared is more specifically illustrated in the following examples.

EXAMPLE 1

Preparation of 5-(2-Chloro-4-trifluoromethylphenoxy)-2-(methylthio)-phenol 3-(2-Chloro-4-trifluoromethylphenoxy)phenol (30 grams) and methylene chloride (150 ml) were charged into a glass reaction vessel equipped with a mechanical stirrer and addition funnel. The mixture was stirred until dissolved and cooled to −20° C. Eighty ml of the solution of methyl sulfenyl chloride freshly prepared by reacting dimethyl disulfide (9.6 grams) with chlorine (6 grams) in methylene chloride (100 ml) was then added dropwise to the reaction vessel over a period of 45 minutes. After the addition was completed stirring was continued for 30 minutes at −20° C. and thereafter for 30 minutes at room temperature. After this time the reaction mixture was washed with water (200 ml), with 5% aqueous sodium bicarbonate (200 ml) and again with water (200 ml). The washed solution was dried by passing it through a phase separator and was then stripped of solvent under aspirator pressure leaving a dark orange oil (30.2 grams). This oil was subjected to distillation and the fractions boiling above 145° C. at 1 mm Hg pressure were collected and combined. The distillate was then subjected to chromatography using a clay column and mixtures of hexane and ethyl acetate as the eluant. Thirteen fractions were collected. Fractions 3 to 10 were combined and stripped of solvents to yield the desired product 5-(2-chloro-4-trifluoromethylphenoxy)-2-(methylthio)phenol as the residue.

EXAMPLE 2

Preparation of Ethyl 2-[5-(2-Chloro-4-trifluoromethylphenoxy)-2-methylthiophenoxy]propionate 5-(2-Chloro-4-trifluoromethylphenoxy)-2-(methylthio)phenol (9.5 grams; 0.0296 mole), potassium carbonate (16.56 grams; 0.12 mole) ethyl 2-bromopropionate (7.79 ml; 0.06 mole) and dimethylsulfoxide (150 ml) were charged into a glass reaction vessel equipped with a mechanical stirrer. The mixture was stirred at room temperature for a period of about 7 hours. After this time the reaction mixture poured into 600 ml of water. The resulting mixture was then extracted three times with 100 ml portions of methylene chloride. The extracts were combined and washed with water. The washed extract was then dried using a phase separator. The dried solution was stripped of solvent under aspirator pressure leaving a clear oil as the residue. The residue was chromatographed through a clay column using hexane and ethyl acetate as the eluant. Fourteen fractions were collected and fraction 12 was stripped of solvents to yield the desired product ethyl 2-[5-(2-chloro-4-trifluoromethylphenoxy)-2-methylthiophenoxy]propionate as a white crystalline solid melting at 70° to 71° C.

EXAMPLE 3

Preparation of 5-(2-Bromo-4-nitrophenoxy)-2-(methylthio)phenol 3-(2-Bromo-4-nitrophenoxy)phenol (0.01 mole) and methylene chloride (200 ml) are charged into a glass reaction vessel equipped with a mechanical stirrer and addition funnel. The mixture is stirred until dissolved and cooled to about −20° C. A solution of methyl sulfenyl chloride freshly prepared by reacting dimethyl disulfide (0.015 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml) with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(2-bromo-4-nitrophenoxy)-2-(methylthio)phenol as the residue.

EXAMPLE 4

Preparation of Ethyl 2-[5-(2-Bromo-4-nitrophenoxy)-2-methylthiophenoxy]propionate 5-(2-Bromo-4-nitrophenoxy)-2-(methylthio)phenol (0.05 mole) potassium carbonate (0.2 mole), ethyl 2-bromopropionate (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined, washed with water and thereafter dried. The dried solution is then stripped of solvent under reduced pressure to leave a residue. The residue is subjected to chromatography using a clay column and hexane/ethyl acetate mixtures as the eluant. The fractions containing the product are combined and stripped of solvent to yield the desired product ethyl-2-[5-(2-bromo-4-nitrophenoxy)-2-methylthiophenoxy]propionate as the residue.

EXAMPLE 5

Preparation of 5-(2-Chloro-4-cyanophenoxy)-2-(ethylthio)phenol 3-(2-chloro-4-cyanophenoxy)phenol (0.01 mole) and methylene chloride (200 ml) are charged into a glass reaction vessel equipped with a mechanical stirrer and addition funnel. The mixture is stirred until dissolved and cooled to about −20° C. A solution of ethyl sulfenyl chloride freshly prepared by reacting diethyl disulfide (0.15 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml), with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(2-chloro-4-cyanophenoxy)-2-(ethylthio)phenol as the residue.

EXAMPLE 6

Preparation of S-Methyl 2-[5-(2-Chloro-4-cyanophenoxy)-2-ethylthiophenoxy]thiolopropionate 5-(2-Chloro-4-cyanophenoxy)-2-(ethylthio)phenol (0.05 mole) potassium carbonate (0.2 mole), S-methyl 2-bromothiolopropionate (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined with water and thereafter dried. The dried solution is then stripped of solvent under reduced pressure to leave a residue. The residue is subjected to chromatography using a clay column and hexane/ethyl acetate mixtures as the eluant. The fractions containing the product are combined and stripped of solvent to yield the desired product S-methyl 2-[5-(2-chloro-4-cyanophenoxy)-2-ethylthiophenoxy]thiolopropionate as the residue.

EXAMPLE 7

Preparation of
5-(2,4-Dichlorophenoxy)-2-(propylthio)phenol 3-(2,4-Dichlorophenoxy)phenol (0.1 mole) and methylene chloride (200 ml) are charged into a glass reaction vessel equipped with a mechanical stirrer and addition funnel. The mixture is stirred until dissolved and cooled to about $-20°$ C. A solution of propyl sulfenyl chloride freshly prepared by reacting dipropyl disulfide (0.15 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml), with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(2,4-dichlorophenoxy) 2-(propylthio)phenol as the residue.

EXAMPLE 8

Preparation of
N,N-Dimethyl-2-[5-(2,4-dichlorophenoxy)-2-propylthiophenoxy]propionamide 5-(2,4-Dichlorophenoxy)-2-(propylthio)phenol (0.05 mole), potassium carbonate (0.2 mole), N,N-dimethyl 2-bromopropionamide (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined, washed with water and therafter dried. The dried solution is then stripped of solvent under reduced pressure to leave a residue. The residue is subjected to chromatography using a clay column and hexane/ethyl acetate mixtures as the eluant. The fractions containing the product are combined and stripped of solvent to yield the desired product N,N-dimethyl-2-[5-(2,4-dichlorophenoxy)-2-propylthiophenoxy]propionamide as the residue.

EXAMPLE 9

Preparation of 5-(2-Nitro-4-trifluoromethylphenoxy) 2-methylthiophenol 3-(2-Nitro-4-trifluoromethylphenoxy)phenol (0.1 mole) and methylene chloride (200 ml) are charged into a glass reaction vessel equipped with a mechanical stirrer and addition funnel. The mixture is stirred until dissolved and cooled to about $-20°$ C. A solution of methyl sulfenyl chloride freshly prepared by reacting dimethyl disulfide (0.15 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml), with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(2-nitro-4-trifluoromethylphenoxy) 2-(methylthio)phenol as the residue.

EXAMPLE 10

Preparation of Propyl
2-[5-(2-Nitro-4-trifluoromethylphenoxy)-2-methylthiophenoxy]propionate 5-(2-Nitro-4-trifluoromethylphenoxy)-2-(methylthio)phenol (0.05 mole), potassium carbonate (0.2 mole), propyl 2-bromopropionate (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined, washed with water and thereafter dried. The dried solution is then stripped of solvent under reduced pressure to leave a residue. The residue is subjected to chromatography using a clay column and hexane/ethyl acetate mixtures as the eluant. The fractions containing the product are combined and stripped of solvent to yield the desired product propyl 2-[5-(2-nitro-4-trifluoromethylphenoxy)-2-methylthiophenoxy]propionate as the residue.

EXAMPLE 11

Preparation of
5-(2-Cyano-4-fluorophenoxy)-2-methylthiophenol 3-(2-Cyano-4-fluorophenoxy)phenol (0.1 mole) and methylene chloride (200 ml) are charged into a glass reaction vessel equipped with a mechanical stirrer and addition funnel. The mixture is stirred until dissolved and cooled to about $-20°$ C. A solution of methyl sulfenyl chloride freshly prepared by reacting dimethyl disulfide (0.15 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml) with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(2-cyano-4-fluorophenoxy) 2-(methylthio)-phenol as the residue.

EXAMPLE 12

Preparation of 2-[5-(2-Cyano-4-fluorophenoxy)-2-methylthiophenoxy]propionamide 5-(2-Cyano-4-fluorophenoxy)-2-(methylthio)phenol (0.05 mole) potassium carbonate (0.2 mole), 2-bromopropionamide (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined, washed with water and thereafter dried. The dried solution is then stripped of solvent under reduced pressure to leave a residue. The residue is subjected to chromatography using a clay column and hexane/ethyl acetate mixtures as the eluant. The fractions containing the product are combined and stripped of solvent to yield the desired product 2-[5-(2-cyano-4-fluorophenoxy)-2-methylthiophenoxy]propionamide as the residue.

EXAMPLE 13

Prepration of 5-(4-Bromophenoxy)-2-(methylthio)phenol 3-(4-Bromophenoxy)phenol (0.1 mole) and methylene chloride (200 ml) are charged into a glass reaction vessel equipped with a mechanical stirrer and addition funnel. The mixture is stirred until dissolved and cooled to about −20° C. A solution of methyl sulfenyl chloride freshly prepared by reacting dimethyl disulfide (0.15 mole) with chlorine (0.18 mole) in methylene chloride (100 ml) is then added dropwise to the reaction vessel over a period of about 40 minutes. After the addition is completed stirring is continued for 30 minutes with cooling and 30 minutes at room temperature. After this time the reaction mixture is washed with water (200 ml), with 5% aqueous sodium bicarbonate (200 ml) and again with water (200 ml). The washed solution is then dried by passing it through a phase separator. The dried solution is stripped of solvent under reduced pressure and the residue chromatographed using a clay column and hexane/ethyl acetate as the eluant. The fractions containing the product are combined and stripped of solvent to yield the desired product 5-(4-bromophenoxy) 2-(methylthio)phenol as the residue.

EXAMPLE 14

Preparation of Methyl 2-[5-(4-Bromophenoxy)-2-methylthiophenoxy]acetate 5-(4-Bromophenoxy)-2-(methylthio)phenol (0.05 mole), potassium carbonate (0.2 mole), methyl 2-bromoacetate (0.08 mole) and dimethylsulfoxide (200 ml) are charged into a 500 ml glass reaction flask equipped with a mechanical stirrer. The reaction mixture is stirred at room temperature for a period of about 8 hours. After this time the mixture is poured into 500 ml of water. The resulting mixture is extracted three times with 100 ml portions of methylene chloride. The extracts are then combined, washed with water and theraftjer dried. The dried solution is then stripped of solvent under reduced pressure to leave a residue. The residue is subjected to chromatography using a clay column and hexane/ethyl acetate mixture as the eluant. The fractions containing the product are combined and stripped of solvent to yield the desired product methyl 2-[5-(4-bromophenoxy)-2-methylthiophenoxy]acetate as the residue.

EXAMPLE 15

Preparation of the Sodium Salt of 2-[5-(2-Chloro-4-trifluoromethylphenoxy)-2-methylthiophenoxy]propionic Acid 2-[5-(2-Chloro-4-trifluoromethylphenoxy)-2-methylthiophenoxy]propionic acid (0.05 mole), ethanol (100 ml) and sodium hydroxide (0.05 mole) are charged into a glass reaction vessel equipped with a mechanical stirrer. The reaction mixture is warmed on a steam bath and stirred for a period of about 1 hour. After this time the mixture is stripped of ethanol and the residue is triturated in ether. The residue is recovered by filtration and is dried to yield the desired product sodium salt of 2-[5-(2-chloro-4-trifluoromethylphenoxy)-2-methylthiophenoxy]propionic acid.

EXAMPLE 16

Preparation of the Ammonium Salt of 2-[5-(2-Bromo-4-nitrophenoxy)-2-methylthiophenoxy]propionic Acid 2-[5-(2-Bromo-4-nitrophenoxy)-2-methylthiophenoxy]propionic acid (0.05 mole) dissolved in ether (100 ml) is charged into a glass reaction vessel equipped with a mechanical stirrer and gas inlet tube. The solution is stirred and ammonia gas (0.1 mole) is bubbled into the solution. After the addition is completed stirring is continued for a period of about 1 hour. After this time the reaction mixture is stripped of ether leaving the desired product sodium salt of 2-[5-(2-chloro-4-trifluoromethylphenoxy)-2-methylthiophenoxy]propionic acid as the residue.

EXAMPLE 17

Preparation of the Dimethylamine Salt of 2-[5-(2-chloro-4-trifluoromethylphenoxy)-2-methylthiophenoxy]propionic Acid 2-[5-(2-chloro-4-trifluoromethylphenoxy)-2-methylthiophenoxy]propionic acid (0.05 mole), an aqueous solution of dimethylamine (0.05 mole; 40% concentration) and water (50 ml) are charged into a glass reaction vessel equipped with a mechanical stirrer. The mixture is stirred at room temperature for a period of about 30 minutes. After this time the mixture is stripped of water under reduced pressure to yield the desired product dimethylamine salt of 2-[5-(2-chloro-4-trifluoromethylphenoxy)-2-methylthiophenoxy]propionic acid as the residue.

Additional compounds within the scope of the present invention which can be prepared by the procedures described in the foregoing examples include methyl 2-[5-(2-chloro-4-trifluoromethylphenoxy)-2-ethylthiophenoxy]propionate, methyl 2-[5-(2-chloro-4-trifluoromethylphenoxy)-2-propylthiophenoxy]propionate, methyl 2-[5-(2-chloro-4-trifluoromethylphenoxy)-2-butylthiophenoxy]propionate, methyl 2-[5-(2-chloro-4-trifluoromethylphenoxy)-2-hexylthiophenoxy]propionate, ethyl 2-[5-(2-chloro-4-trifluoromethylphenoxy)-2-methylthiophenoxy]propionate, propyl 2-[5-(2-chloro-4-trifluoromethylphenoxy)-2-methylthiophenoxy]propionate, propyl 2-[5-(2-chloro-4-trifluoromethylphenoxy)-2-methylthiophenoxy]propionamide, N- methyl-2-[5-(2-chloro-4-trifluoromethylphenoxy)-2-ethylthiophenoxy]propionamide, N-ethyl-2-[5-(2-chloro-4-trifluoromethylphenoxy)-2-ethylthiophenoxy]propionamide, N-propyl-2-[5-(2-chloro-4-trifluoromethylphenoxy)-2-methylthiophenoxy]propionamide, N-hexyl-2-[5-(2-chloro-4-trifluoromethylphenoxy)-2-methylthiophenoxy]propionamide, N,N-dimethyl 2-[5-(2-chloro-4-trifluoromethylphenoxy)-2-methylthiophenoxy]propionamide, N,N-diethyl-2-[5-(2-chloro-4-trifluoromethylphenoxy)-2-methylthiophenoxy]propionamide, N,N-dihexyl-2-[5-(2-chloro-4-trifluoromethylphenoxy)-2-methylthiophenoxy]propionamide, S-methyl 2-[5-(2-chloro-4-trifluoromethylphenoxy)-2-methylthiophenoxy]thiopropionate, S-ethyl 2-[5-(2-chloro-4-trifluoromethylphenoxy)-2-methylthiophenoxy]thiopropionate, S-propyl 2-[5-(2-chloro-4-trifluoromethylphenoxy)-2-methylthiophenoxy]thiopropionate, S-hexyl 2-[5-(2-chloro-4-trifluoromethylphenoxy)-2-methylthiophenoxy]thiopropionate, methyl 2-[5-(2-chloro-4-trifluoromethylphenoxy)-2-methylthiophenoxy]butyrate, methyl 2-[5-(2-chloro-4-trifluoromethylphenoxy)-2-methylthiophenoxy]pantanoate, methyl 2-[5-(2-chloro-4-trifluoromethylphenoxy)-2-methylthiophenoxy]hexanoate, methyl 2-[5-(2-chloro-4-trifluoromethylphenoxy)-2-methylthiophenoxy]heptanoate, methyl 2-[5-(2-bromo-4-trifluoromethylphenoxy)-2-methylthiophenoxy]propionate,سsodium 2-[5-(2-chloro-4-trifluoromethylphenoxy)-2-methylthiophenoxy]propionate, potassium 2-[5-(2-chloro-4-trifluoromethylphenoxy)-2-methylthiophenoxy]propionate, lithium 2-[5-(2-chloro-4-trifluoromethylphenoxy)-2-methylthiophenoxy]propionate, calcium 2-[5-(2-chloro-4-trifluoromethylphenoxy)-2-methylthiophenoxy]propionate, methylamine salt of 2-[5-(2-chloro-4-trifluoromethylphenoxy)-2-methylthiophenoxy]propionic acid, dimethylamine salt of 2-[5-(2-chloro-4-trifluoromethylphenoxy)-2-methylthiophenoxy]propionic acid, triethylamine salt of 2-[5-(2-chloro-4-trifluoromethylphenoxy)-2-methylthiophenoxy]propionic acid, methanolamine salt of 2-[5-(2-chloro-4-trifluoromethylphenoxy)-2-methylthiophenoxy]propionic acid, ethanolamine salt of 2-[5-(2-chloro-4-trifluoromethylphenoxy)-2-methylthiophenoxy]propionic acid, hexylamine salt of 2-[5-(2-chloro-4-trifluoromethylphenoxy)-2-methylthiophenoxy]propionic acid.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 18

Preparation of a Dust

Product of Example 2: 10
Powdered Talc: 90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPP, 2,4,5-TB, 2,4,5-TES, 3,4-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)-morpholine, 1-(chloracetyl) piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidin, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocyil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotwed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was set and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following data set out in Table I. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 10 to 15 days after treatment and was rated on the scale of from 0 to 10 heretobefore described. The effectiveness of these compounds is demonstrated by the following data set forth in Table II. Values with decimal places again are the result of averaging of repliacte experiments.

TABLE I

14 & 21-Day Pre-Emergence Screen

| Compound | #/Acre | JMWD 14 | JMWD 21 | VTLF 14 | VTLF 21 | PIGW 14 | PIGW 21 | WMSD 14 | WMSD 21 | MNGY 14 | MNGY 21 |
|---|---|---|---|---|---|---|---|---|---|---|---|
| Product of | 8 | 10 | 10 | NE | 9 | NE | NE | 10 | 10 | 9 | 8 |
| Example 2 | 4 | NE | NE | 8 | 5 | 9 | NE | NE | NE | 5 | 5 |
|  | 2 | 5 | 0 | 8 | 0 | 8 | 7 | NE | NE | 5 | 4 |
|  | 1 | 0 | 0 | NE | 9 | 0 | 0 | NE | NE | 2 | 0 |

| Compound | #/Acre | WOAT 14 | WOAT 21 | JNGS 14 | JNGS 21 | YLFX 14 | YLFX 21 | BNGS 14 | BNGS 21 | CBGS 14 | CBGS 21 | CTGS 14 | CTGS 21 | YNSG 14 | YNSG 21 |
|---|---|---|---|---|---|---|---|---|---|---|---|---|---|---|---|
| Product of | 8 | 2 | 4 | 9 | 10 | 9 | 9 | 10 | 10 | 9 | 9 | 9 | 10 | 8 | 8 |
| Example 2 | 4 | 0 | 0 | 8 | 8 | 8 | 9 | 6 | 0 | 9 | 0 | NE | 8 | 6 | 3 |
|  | 2 | 0 | 0 | 8 | 8 | 7 | 4 | 5 | 0 | 5 | 0 | 7 | 8 | 0 | 0 |
|  | 1 | 0 | 0 | 7 | 5 | 0 | 0 | 2 | 0 | 8 | 0 | NE | NE | 0 | 0 |

Abbreviations For Weeds

| | | | |
|---|---|---|---|
| WMSD | = Wild Mustard | COTN | = Cotton |
| BDWD | = Bindweed | SOYB | = Soybean |
| PIGW | = Pigweed | PTBN | = Pintobean |
| JMWD | = Jimsonweed | ALFA | = Alfalfa |
| VTLF | = Velvetleaf | SORG | = Sorgum |
| MNGY | = Morningglory | WHT | = Wheat |
| YLFX | = Yellow Foxtail | PSDA | = Prickley Sida |
| BNGS | = Barnyardgrass | CKBR | = Cocklebur |
| JNGS | = Johnsongrass | IVMNGY | = Ivyleaf Morningglory |
| QKGS | = Quackgrass | CDCK | = Curlydock |
| WOAT | = Wild Oat | WMSTD | = Wild Mustard |
| CBGS | = Crabgrass | SKPD | = Sicklepod |
| SPGT | = Sprangletop | ANNGY | = Annual Morningglory |
| CTGS | = Cheatgrass | YNSG | = Yellownutsedge |
| SUBT | = Sugarbeet | | |

TABLE II

Post-Emergence Screen

| Compound | #/Acre | WMSD | BDWD | PIGW | JMWD | VTLF | MNGY | YLFX | BNGS | JNGS | QKGS | WOAT |
|---|---|---|---|---|---|---|---|---|---|---|---|---|
| Product of | 8 | 10 | 10 | 10 | — | — | 10 | 10 | 10 | 10 | — | 4 |
| Example 2 | 2 | 10 | 10 | 10 | — | — | 10 | 4 | 6 | 9 | — | 2 |
|  | 1 | 10 | 10 | 10 | 10 | — | 10 | 3 | 3 | 7 | — | 2 |
|  | .5 | 10 | 10 | — | 10 | 10 | 10 | 1* | 1* | 1.5* | 5* | 4* |
|  | .25 | 10 | 10 | — | 10 | 10 | 10 | 0 | 0 | 0 | 0 | 1 |
|  | .125 | 10 | 8* | — | — | 10 | 10 | 0 | 0 | 0 | 0 | 7 |
|  | .062 | 10 | 6* | — | — | 9.5* | 10 | 0 | 0 | 0 | 0 | 0 |
|  | .031 | — | 2 | — | 10 | 10 | — | — | — | — | — | — |
|  | .015 | — | 2 | — | 5 | 4 | — | — | — | — | — | — |

| Compound | #/Acre | CBGS | SPGT | CTGS | SUBT | COTN | SOYB | PTBN | ALFA | SORG | WHT | RICE | CORN | OAT |
|---|---|---|---|---|---|---|---|---|---|---|---|---|---|---|
| Product of | 8 | 10 | — | — | — | — | 10 | — | — | — | — | — | — | — |
| Example 2 | 2 | 3 | — | — | — | — | 10 | — | — | — | — | — | — | — |
|  | 1 | 0 | — | — | — | — | 6 | — | — | — | — | — | — | — |
|  | .5 | 0 | 0 | 0 | 10 | 10 | 7* | 10 | 10 | 1 | 0 | 0 | 0 | 8 |
|  | .25 | 0 | 0 | 0 | 10 | 10 | 3 | 10 | 10 | 0 | 0 | 0 | 0 | 0 |
|  | .125 | 0 | 0 | 0 | 10 | 10 | 2.5* | 10 | 10 | 0 | 0 | 0 | 0 | 7 |
|  | .062 | 0 | 0 | 0 | — | 10 | 1.5* | 10 | 10 | 0 | 0 | 0 | 0 | 0 |
|  | .031 | — | — | — | — | — | — | — | — | — | — | — | — | — |
|  | .015 | — | — | — | — | 1 | — | — | — | — | — | — | — | — |

| Compound | #/Acre | PSDA | CKBR | RAPE | IVMNGY | CDCK | WMSTD | SKPD | ANNGY | YNSG |
|---|---|---|---|---|---|---|---|---|---|---|
| Product of | 8 | — | — | — | — | — | — | — | — | 1 |
| Example 2 | 2 | — | — | — | — | — | — | — | — | 0 |
|  | 1 | — | — | — | — | — | — | — | — | 0 |
|  | .5 | — | — | — | — | — | — | — | — | 0 |
|  | .25 | — | — | — | — | — | — | — | — | — |
|  | .125 | 2 | 3 | 10 | 10 | 3 | 2 | 1 | 4 | — |
|  | .062 | 2 | 2 | 7 | 10 | 0 | 1 | 1 | 3 | — |
|  | .031 | 1 | 0 | 1 | 4 | 0 | 2 | 0 | 3 | — |
|  | .015 | 1 | — | 2 | — | 2 | 3 | 1 | 0 | 1 | — |

* = Average of two tests

I claim:

1. A compound of the formula:

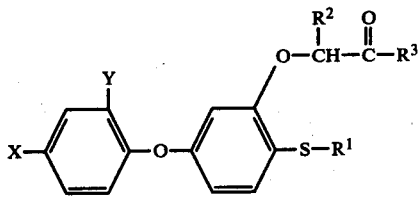

wherein X is selected from the group consisting of halogen, nitro, cyano and trifluoromethyl; Y is selected from the group consisting of hydrogen, halogen, nitro and cyano; $R^1$ is lower alkyl; $R^2$ is selected from the group consisting of hydrogen and lower alkyl; and $R^3$ is selected from the group consisting of hydroxy, lower alkoxy, lower alkylthio, amino, lower alkylamino and di(loweralkyl)amino.

2. An alkali metal, alkaline earth metal, ammonium, amine, lower alkylamine, di(loweralkyl)amine, lower alkanolamine, di(loweralkanol)amine or tri(loweralkanol)amine salt of a compound of claim 1 wherein $R^3$ is hydroxy.

3. The compound of claim 1, ethyl 2-[5-(2-chloro-4-trifluoromethylphenoxy)-2-methylthiophenoxy]priopionate.

4. The compound of claim 1, ethyl 2-[5-(2-bromo-4-nitrophenoxy)-2-(methylthio)phenoxy]propionate.

5. The compound of claim 1, S-methyl 2-[5-(2-chloro-4-cyanophenoxy)-2-(ethylthio)phenoxy]thiolopropionate.

6. The compound of claim 1, N,N-dimethyl-2-[5-(2,4-dichlorophenoxy)-2-(propylthio)phenoxy]propionamide.

7. The compound of claim 1, propyl 2-[5-(2-nitro-4-trifluoromethylphenoxy)-2-methylthiophenoxy]propionate.

8. The compound of claim 1, 2-[5-(2-cyano-4-fluorophenoxy)-2-methylthiophenoxy]propionamide.

9. A herbicidal composition consisting essentially of an inert carrier and, in a quantity toxic to weeds, a compound of claim 1.

10. A herbicidal composition consisting essentially of an inert carrier and, in a quantity toxic to weeds, a compound of claim 2.

11. A method of controlling weeds which consists essentially of contacting the weeds or the locus of the weeds with a herbicidally effective amount of a composition of claim 9.

12. A method of controlling weeds which consists essentially of contacting the weeds or the locus of the weeds with a herbicidally effective amount of a composition of claim 10.

* * * * *